(12) United States Patent
Johnson

(10) Patent No.: US 9,074,172 B2
(45) Date of Patent: Jul. 7, 2015

(54) CULTURE PLATE WITH FIBER-COATED BOTTOM SURFACE

(76) Inventor: Jed K. Johnson, Columbus, OH (US)

( * ) Notice: Subject to any disclaimer, the term of this patent is extended or adjusted under 35 U.S.C. 154(b) by 265 days.

(21) Appl. No.: 13/590,244

(22) Filed: Aug. 21, 2012

(65) Prior Publication Data
US 2014/0057346 A1 Feb. 27, 2014

(51) Int. Cl.
*C12M 1/22* (2006.01)
*C12M 3/00* (2006.01)
*C12M 1/32* (2006.01)
*C12M 1/00* (2006.01)

(52) U.S. Cl.
CPC ............... *C12M 23/12* (2013.01); *C12M 23/20* (2013.01)

(58) Field of Classification Search
CPC .............................. C12M 23/12; C12M 23/20
USPC ............................................. 435/283.1–309.4
See application file for complete search history.

(56) References Cited

U.S. PATENT DOCUMENTS

| | | | | |
|---|---|---|---|---|
| 6,218,178 B1* | 4/2001 | Banes | ................... | 435/305.1 |
| 6,472,202 B1* | 10/2002 | Banes | ................... | 435/305.1 |
| 2005/0047971 A1* | 3/2005 | Clements et al. | ............ | 422/102 |
| 2005/0266478 A1* | 12/2005 | Huang et al. | ................... | 435/6 |
| 2010/0119418 A1* | 5/2010 | Clements et al. | ............ | 422/102 |
| 2010/0311614 A1* | 12/2010 | Montagu et al. | ................ | 506/14 |
| 2012/0129713 A1* | 5/2012 | Montagu et al. | ................ | 506/9 |
| 2012/0298288 A1* | 11/2012 | Anderson | ................ | 156/146 |

* cited by examiner

*Primary Examiner* — Nathan Bowers
*Assistant Examiner* — Lydia Edwards
(74) *Attorney, Agent, or Firm* — McNees, Wallce & Nurick, LLC

(57) ABSTRACT

A cell culture plate that includes an upper portion having at least one discrete chamber with a top edge and a bottom edge; a substantially flat lower portion, wherein at least one layer of polymer fibers has been deposited on the upper surface of the lower portion, and wherein the at least one layer of polymer fibers is conducive to the growth of biological cells thereon; and wherein the bottom edge of the at least one discrete chamber is hermetically sealed to the fiber-coated upper surface of the lower portion to form a well using adhesives, laser welding, or ultrasonic welding.

5 Claims, 2 Drawing Sheets

CULTURE PLATE WITH FIBER-COATED BOTTOM SURFACE

BACKGROUND OF THE INVENTION

The described invention relates in general to single and multiwell plates used for cell culture or other purposes, and more specifically to a cell culture plate that includes a bottom portion that has been coated with growth-enhancing polymer fibers and a top portion that has been bonded to the bottom portion in a manner that creates one or more hermetically sealed culturing wells.

Historically, cell culture has been performed in vitro using a variety of containers including glass Petri dishes as well as polystyrene dishes and multiwell plates. Plastic dishes and plates have typically been manufactured by extrusion processes or compression molding to form various shapes and configurations. Recently, more complex culture plates have been produced wherein the bottom culture surface is glass and the sidewalls are polystyrene or polypropylene. Certain relatively advanced adhesives are used to join these dissimilar materials together and form strong, reliable bonds, hopefully without deleteriously affecting cell growth. However, any contaminates or particulate matter found on the bonding surfaces can significantly impair or prevent effective bonding of the two materials. Therefore, significant care must be taken to ensure that mating surfaces are clean before attempting to create a bond between them. While effective bonding may be achieved, the biocompatibility of the adhesives used may not be optimal. Furthermore, the various reagents and other chemicals used in standard cell culture may have a deleterious effect on the integrity of the bonds formed between the materials used in the culture plates and may even leach chemical ingredients out of the adhesive and into the culture well. Therefore, there is an ongoing need for an improved process for effectively joining the components of cell culture plates to one another without negatively affecting cell growth.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first culture plate is provided. This culture plate includes an upper portion, wherein the upper portion further includes at least one discrete chamber having a top edge and a bottom edge; a substantially flat lower portion, wherein at least one layer of polymer fibers has been deposited on the upper or top surface of the lower portion, and wherein the at least one layer of polymer fibers is conducive to the growth of biological cells thereon; and wherein the bottom edge of the at least one discrete chamber is hermetically sealed to the fiber-coated upper surface of the lower portion to form a well.

In accordance with another aspect of the present invention, a second culture plate is provided. This culture plate includes an upper portion, wherein the upper portion further includes at least one discrete chamber having a top edge and a bottom edge; a substantially flat lower portion, wherein at least one layer of polymer fibers has been deposited on the upper or top surface of the lower portion by electrospinning, wherein the at least one layer of polymer fibers is conducive to the growth of biological cells thereon, and wherein the polymer fibers are microscale fibers, nanoscale fibers, or both; and wherein the bottom edge of the at least one discrete chamber is hermetically sealed to the fiber-coated upper surface of the lower portion to form a well.

In yet another aspect of this invention, a third culture plate is provided. This culture plate includes an upper portion, wherein the upper portion further includes at least one discrete chamber having a top edge and a bottom edge, and wherein the bottom edge further includes an energy directing structure formed integrally therewith; a substantially flat lower portion, wherein at least one layer of polymer fibers has been deposited on the upper or top surface of the lower portion, and wherein the at least one layer of polymer fibers is conducive to the growth of biological cells thereon; and wherein the bottom edge of the at least one discrete chamber is hermetically sealed to the fiber-coated upper surface of the lower portion to form a well, and wherein the hermetic seal is created by directing ultrasonic energy through the energy directing structure into the lower portion of the culture plate.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Figure 1A:
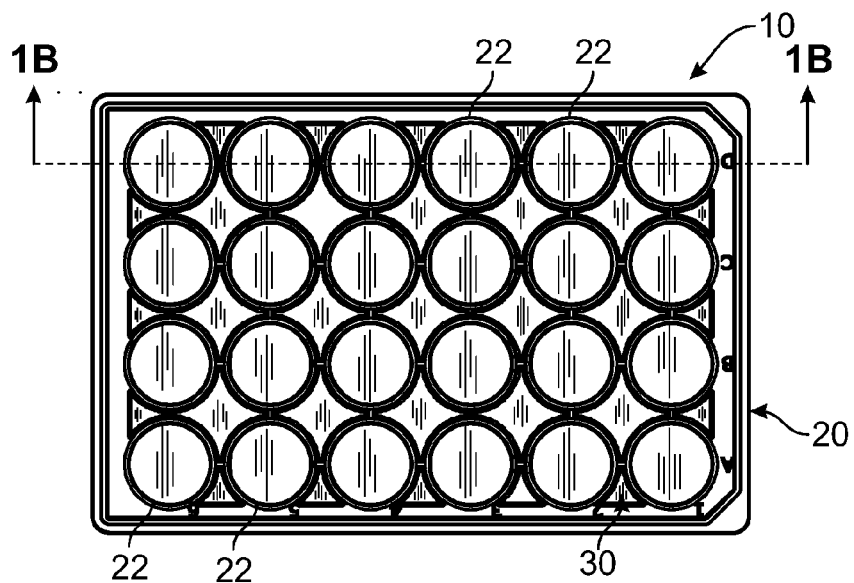
FIGS. 1*a-c* are various views bottom view of a 24-well cell culture plate made in accordance with an exemplary embodiment of the present invention showing high-integrity bonds formed between the bottom and upper portions of the plate.

Exemplary embodiments of the present invention are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention. With reference now to the Figures, one or more specific embodiments of this invention shall be described in greater detail.

Figure 1B:
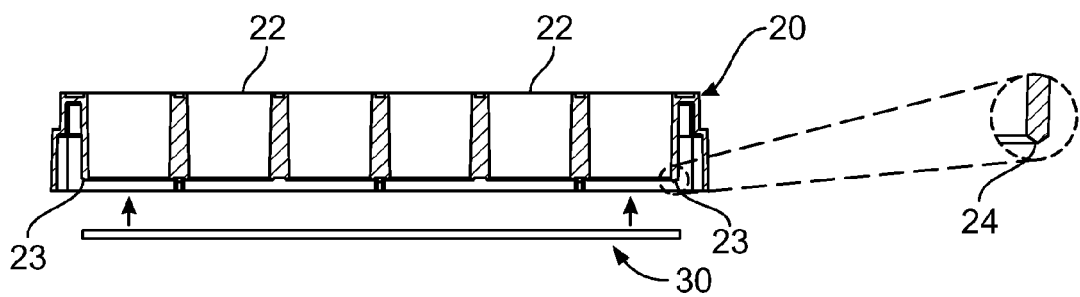
Figure 1C:
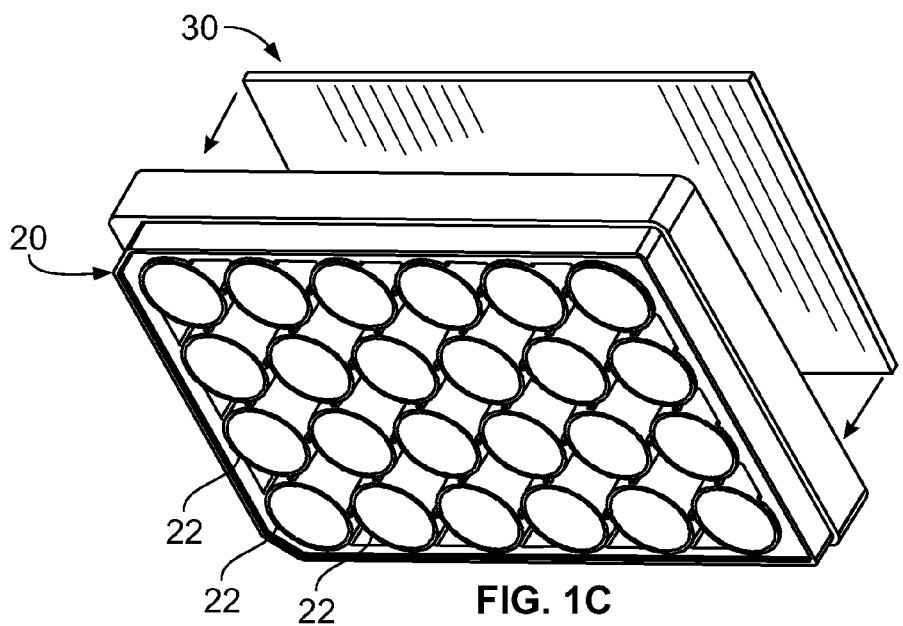

With reference to FIG. 1, in general terms, culture plate 10 includes upper portion 20 and lower portion 30 that are bonded to one another. Both portions are typically manufactured separately from one or more different polymers such as those previously discussed. Upper portion 20 includes one or more discrete (i.e., individual) walled chambers 22 each of which includes a top edge and a bottom edge surrounding the top and bottom openings of the chamber respectively. These walled chambers are typically cylindrical in shape, but other geometries are possible. Lower portion 30 is typically flat or substantially flat and in most embodiments of this invention at least one layer of polymer fibers has been deposited on the upper surface of lower portion 30 prior to bonding the lower portion to the upper portion of the culture plate. These polymer fibers provide a culture surface that is conducive to the growth and/or differentiation of biological cells and that can significantly improve the outcome of any given cell culture experiment. The fibers may be nanoscale (less than 1000 nanometers) and/or microscale (less than 50 microns) polymer fibers and are typically deposited by electrospinning or a similar known process. The orientation of the polymer fibers relative to one another is generally parallel, random, or both. The polymer fibers may include resorbable materials that further include polycaprolactone (PCL), polylactic acid (PLA), polyglycolic acid (PGA), and/or combinations thereof. The polymer fibers may also include materials such as polyethylene terephthalate (PET), polyetherketoneketone (PEKK), polyurethane (PU), polycarbonate (PC), polyamide (Nylon), or combinations thereof. The polymer fibers may also include natural polymers that further include collagen, gelatin, fibronectin, hyaluronic acid, or combinations thereof. Large sheets of polymer film may be coated with polymer fibers, in accordance with this invention, and then the sheets may be cut into smaller sections for use in constructing culture plates. Bottom edge 23 of each walled chamber 22 is hermetically sealed to the fiber-coated upper surface of lower portion 30 to form a well for containing cell culture medium. Hermetic seal 32 (see FIG. 2*b*), which is formed between upper portion 20 and lower portion 30 may be created by various processes including the use of adhesives, laser welding, or ultrasonic welding.

With regard to the use of adhesives, bottom edge 23 of each walled chamber 22 may coated with a suitable adhesive using a fully automated three-axis robot or other means and then brought into contact, under pressure, with the fiber-coated upper surface of an appropriately sized lower portion 30 until a bond is achieved. Suitable adhesives include cyanoacrylate, silicone, epoxy, and UV curable adhesives. The use of adhesives for creating the culture plates of the present invention is effective with fiber layer thicknesses of approximately 50 μm or less.

The use of laser welding eliminates any adhesive from the culture environment and may be utilized to locally heat the mating surfaces and form a strong, permanent bond without melting the polymer fibers on the culture surface. An exemplary approach utilizes a clear glass plate for applying pressure to the mating surfaces while permitting laser energy to pass through and weld the materials together. A 15 kW fiber laser and an optic that produces a wide beam permit making a minimum number of passes to seal an entire well plate. Beam delivery options include a small single spot that can be manipulated around the entire part, a line of light that can be scanned from one side to the other, or an image the size of a given well plate that can be generated using custom optics for simultaneous exposure. The power levels involved increase with each of these delivery methods. In one exemplary method, a diode or fiber laser (808 to 1070 nm) with roughly 750-1000 W and a custom optic for generating a line of light that is as long as the width of a defined weld path was used. The line was scanned from left to right once using a motion table. Laser welding is effective with polymer fiber layer thicknesses of approximately 100 μm thick or less. Additionally, laser welding is effective when upper portion 20 is a dark color such as black that is capable of absorbing the energy of the laser to create localized heating. When using this bonding technique, lower portion 30 should be a clear plastic, fiber coated film. Opaque films may absorb laser energy and prevent bonding.

Figure 2A:
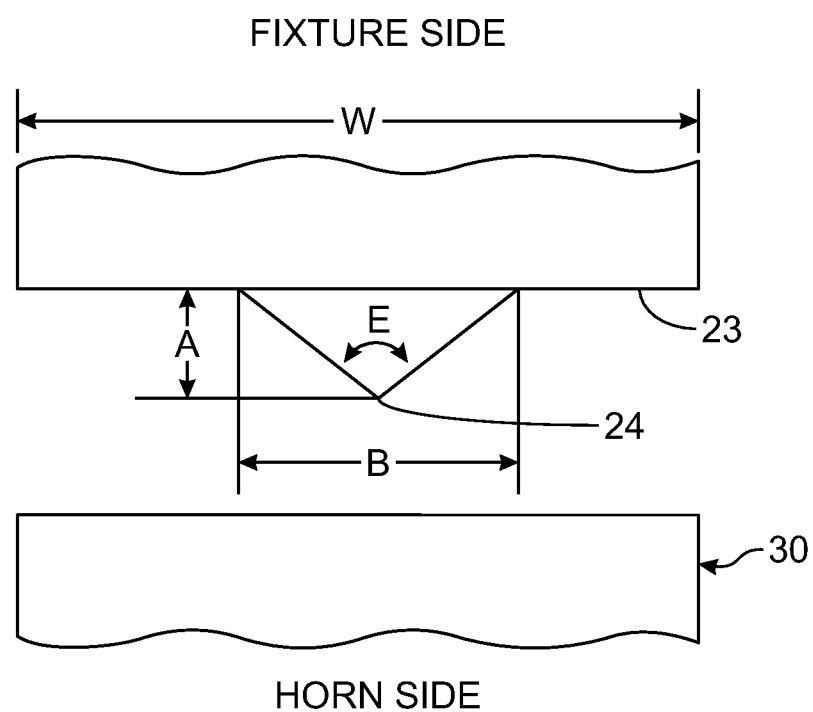
FIG. 2*a* is a diagrammatic representation of one of the energy directing devices included in some embodiments of the present invention.
Figure 2B:
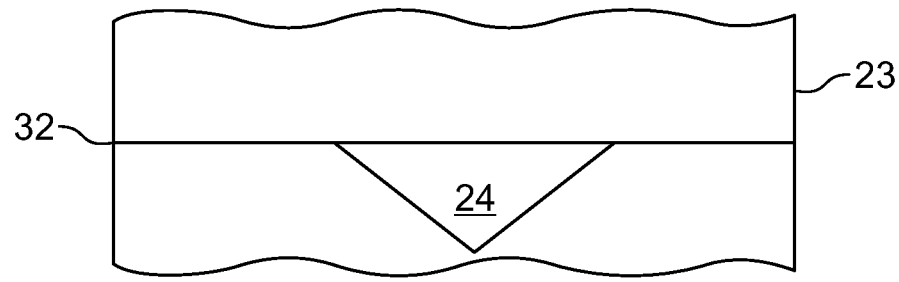
FIG. 2*b* is a diagrammatic representation of the energy directing device of FIG. 2*a* engaging the lower portion of a cell culture plate following the application of ultrasonic energy thereto.

The use of ultrasonic welding eliminates the possibility that heat generated by a laser may melt some of the polymer fibers within a culture well. Additionally, ultrasonic welding is effective for culture plate construction involving a variety of fiber layer thicknesses and a variety of dissimilar materials used for the upper and lower portions of the plate. With reference to FIGS. 2*a-b*, ultrasonic welding is most effective for plate construction when structures referred to as energy directors are formed integrally with bottom edge 23 of each walled chamber 22. FIG. 2*a* illustrates an exemplary embodiment of a triangular (inverted) energy director 24 formed on bottom edge 23 (which has width W) of a walled chamber 22. In the embodiment of FIG. 2*a*, the wall thickness of chamber 22 is a maximum of 0.090 inches (2.29 mm) with a recommended thickness of 0.040 inches (1.02 mm); the base width B of energy director 24 is 0.006-0.030 inches (0.15 mm-0.76 mm) with a recommended width of 0.016 inches (0.41 mm); the height A of energy director 24 is about 0.008 inches (0.20 mm); and the angle of the apex E of energy director 24 is 60-90° with a recommended angle of 90°. An inverted culture plate 10 is placed into an ultrasonic welding apparatus and ultrasonic energy is applied to the bottom side of lower portion 30 from above (the horn side) causing energy director 24 to "collapse" into the material of lower portion 30 (see FIG. 2*b*). This process results in a strong, permanent bond between similar or dissimilar materials that is airtight and water tight and that does not create any of the previously discussed concerns. Custom designed energy directors can be applied to any size plate (e.g., 1, 6, 12, 24, 48, 96, 384 wells) or dish (e.g., 60 mm, 100 mm, 150 mm). A Branson 2000-series, 20-kHz ultrasonic welding system and ultrasonic horn or similar system may be used for manufacturing culture plates in accordance with this embodiment of the present invention. Exemplary ultrasonic welding parameters appear below in Table 1.

TABLE 1

Exemplary ultrasonic welding parameters.

| | Energy | Hold Time | Amplitude | Hold Pressure |
|---|---|---|---|---|
| 6 Well Plate | 140 J | 1 sec | 35 μm | 40 psi |
| 24 Well Plate | 130 J | 1 sec | 35 μm | 80 psi |
| 96 Well Plate | 160 J | 1 sec | 35 μm | 80 psi |
| 384 Well Plate | 170 J | 1 sec | 35 μm | 80 psi |

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A culture plate, comprising:
   (a) an upper portion, wherein the upper portion further includes at least one discrete walled chamber, having a top edge and a bottom edge; wherein the bottom edge of the at least one discrete chamber includes an energy directing structure formed integrally therewith, wherein the energy directing structure is in the shape of an inverted triangle in cross-section, and wherein the angle of the apex of the inverted triangle is about 60° to about 90°;
   (b) a substantially flat lower portion, wherein the lower portion further includes:
      (i) at least one layer of polymer fibers deposited on the upper surface of the lower portion;
      (ii) wherein the polymer fibers have been deposited on the upper surface of the lower portion by electrospinning;
      (iii) wherein the orientation of the polymer fibers relative to one another is generall parallel, or both; and
      (iv) wherein the at least one layer of polymer fibers is conducive to the growth of biological cells thereon; and
   (c) an ultrasonically-created hermetic seal formed between the bottom edge of the at least one discrete chamber and the fiber-coated upper surface of the lower portion, wherein the hermetic seal is formed by applying ultrasonic energy to the lower portion to create a permanent airtight and watertight bond between bottom edge of the at least one discrete chamber and the fiber-coated upper surface of the lower portion of the culture plate, and wherein the hermetic seal formed between the bottom edge of the at least one discrete chamber and the fiber-coated upper surface of the lower portion forms a well for containing cell culture medium.

2. The culture plate of claim 1, wherein the polymer fibers are microscale fibers, nanoscale fibers, or both.

3. The culture plate of claim 1, wherein the polymer fibers further include resorbable materials, and wherein the resorbable materials further include polycaprolactone (PCL), polylactic acid (PLA), polyglycolic acid (PGA), and combinations thereof.

4. The culture plate of claim 1, wherein the polymer fibers further include polyethylene terephthalate (PET), pol yetherketoneketone (PEKK), polyurethane (PU), polycarbonate (PC), polyamide (Nylon), or combinations thereof.

5. The culture plate of claim 1, wherein the polymer fibers further include natural polymers, and wherein the natural polymers further include collagen, gelatin, fibronectin, hyaluronic acid, or combinations thereof.

* * * * *